United States Patent [19]

Drent

[11] Patent Number: 5,344,961
[45] Date of Patent: Sep. 6, 1994

[54] CARBONYLATION PROCESS

[75] Inventor: Eit Drent, Amsterdam, Netherlands

[73] Assignee: Shell Oil Company, Houston, Tex.

[21] Appl. No.: 70,001

[22] Filed: May 27, 1993

Related U.S. Application Data

[63] Continuation of Ser. No. 974,442, Nov. 12, 1992, abandoned.

[30] Foreign Application Priority Data

Nov. 21, 1991 [EP] European Pat. Off. ........ 91203065.7

[51] Int. Cl.$^5$ ...................... C07C 69/76; C07C 51/10
[52] U.S. Cl. .................... 560/103; 560/105; 562/406
[58] Field of Search ................. 560/103, 105; 562/406

[56] References Cited

U.S. PATENT DOCUMENTS

| | | | |
|---|---|---|---|
| 3,116,306 | 12/1963 | Heck et al. | 260/410.9 |
| 3,988,358 | 10/1976 | Heck | 260/465 D |
| 4,060,690 | 11/1977 | Chahawi et al. | 560/55 |
| 4,128,554 | 12/1978 | Heck | 546/317 |
| 4,128,572 | 12/1978 | Cassar et al. | 562/406 |
| 4,424,394 | 1/1984 | Schneider et al. | 562/406 |
| 4,575,561 | 3/1986 | Sawicki | 562/406 |
| 4,713,484 | 12/1987 | Epstein | 562/406 |
| 4,866,200 | 9/1989 | Rule et al. | 560/80 |
| 5,087,731 | 2/1992 | Huser | 560/103 |
| 5,107,053 | 4/1992 | Wu | 560/105 |

FOREIGN PATENT DOCUMENTS

| | | |
|---|---|---|
| 0248074B1 | 9/1987 | European Pat. Off. |
| 0283194 | 9/1988 | European Pat. Off. |
| 0352167 | 1/1990 | European Pat. Off. |
| 0365382 | 4/1990 | European Pat. Off. |
| 365383 | 4/1990 | European Pat. Off. |
| 0406848A1 | 4/1991 | European Pat. Off. |

*Primary Examiner*—Paul J. Killos

[57] ABSTRACT

An improved process for the carbonylation of aryl halides comprises contacting the aryl halide with carbon monoxide under carbonylation conditions in the presence of a co-reactant, a base, and a catalyst system formed from a source of palladium and a bidentate phosphine ligand wherein at least one monovalent phosphorus substituent is aromatic and is substituted on at least one aromatic ring carbon atom with an electron-withdrawing group.

11 Claims, No Drawings

CARBONYLATION PROCESS

This is a continuation of application Ser. No. 974,442, filed Nov. 12, 1992.

FIELD OF THE INVENTION

The present invention relates to the carbonylation of aryl halides by contact with carbon monoxide in the presence of a co-reactant, a base and a catalyst complex comprising palladium and a bidentate ligand of phosphorus of defined structure.

BACKGROUND OF THE INVENTION

The carbonylation of aryl bromide or aryl iodide to produce products such as an aryl aldehyde, acid or ester derivative is broadly known. U.S. Pat. No. 4,128,554 and U.S. Pat. No. 3,988,358 disclose the use of a palladium-containing catalyst system optionally containing a triarylphosphine. The use of an aryl chloride would offer economic advantages since the chloride is typically cheaper than the bromide or iodide. Catalyst systems for carbonylation of aryl chlorides are disclosed by a number of published European Patent Applications including EP 352167 wherein palladium-containing catalyst systems also include tertiary mono-phosphines. EP-A-238194 illustrates the use of a bidentate phosphine ligand such as 1,4-bis(diphenylphosphino)propane. EP-A-406848 shows aliphatic-and aromatic-substituted diphosphines used in conjunction with palladium. At least one of the monovalent phosphorus substituents is aliphatic.

Although these references do teach formation of aryl derivatives by carbonylation of aryl halides, and even aryl chlorides, it would be of advantage to have an improved process wherein aryl halides are carbonylated at attractive reaction rates.

SUMMARY OF THE INVENTION

The present invention provides an improved process for the production of aroyl derivatives by carbonylation of aryl halide under carbonylation conditions in the presence of a hydrogen-containing co-reactant, a base and a catalyst system formed from a source of palladium and a bidentate ligand of phosphorus substituents in an aromatic group with at least one election-withdrawing substituent. The use of this catalyst system of the invention provides an increase in rates of aryl chloride carbonylation when compared with the catalyst systems containing other phosphine ligands.

DESCRIPTION OF THE INVENTION

The invention is the carbonylation of aryl halide in the carbonylation of aryl halide under carbonylation conditions in the presence of a co-reactant, a base and a catalyst system formed from a source of palladium and an aromatic bidentate phosphine ligand wherein at least one monovalent phosphorus substituent is aromatic and substituted on an aromatic ring carbon atom with an electron-withdrawing substituent.

The aryl halide is an aromatic moiety of up to 20 carbon atoms and up to 2 aromatic rings inclusive. The halide moiety is chlorine, bromine or iodine and aryl chlorides, aryl bromides and aryl iodides are suitable as reactants in the present process. Aryl bromides and aryl iodides are relatively easy to carbonylate in the presence of a variety of catalyst systems so that the process of the invention is most advantageously applied to the carbonylation of aryl chloride. The aryl moiety is hydrocarbyl containing only atoms of carbon and hydrogen in addition to the halogen atom or is substituted hydrocarbyl containing other atoms in the form of inert, ring-carbon atom substituents such as alkoxy or dialkylamino. Illustrative of aryl moieties are aryl groups of one aromatic ring such as phenyl, tolyl, xylyl, methoxyphenyl or dimethylaminophenyl, aryl groups of two fused aromatic rings such as naphthyl, 4-ethylnaphthyl and 5-methoxynaphthyl and aryl groups connected by a valence bond or a connecting alkylene group such as biphenyl, 4'-methylbiphenyl, 2-phenyl-2-methylphenylpropane and diphenylmethane.

Preferred aryl halides are hydrocarbyl aryl halides of one aromatic ring and most preferred as the aryl halide is chlorobenzene.

The co-reactant of the present process comprises a nucleophilic moiety to which a hydrogen is bonded. Such materials include water, ammonia, alkanol of up to 4 carbon atoms, glycol of up to 4 carbon atoms, phenols of up to 15 carbon atoms and up to 2 phenolic hydroxyl groups inclusive, and primary and secondary amines of up to 15 carbon atoms and up to 2 amino groups inclusive. Suitable alkanols include methanol, ethanol, isopropanol, n-butanol and sec-butanol. Glycols are illustrated by ethylene glycol, 1,2-propylene glycol and 1,3-propylene glycol. Phenols useful in the process of the invention are exemplified by phenol, naphthol, 4,4"-biphenol and 2,2-di(4-hydroxyphenyl)methane. Useful amines include n-butylamine, diethylamine, aniline, ethylene diamine and diphenylamine. The preferred co-reactants are hydrogen and alkanol, which lead to the production of aldehydes and alkyl esters, respectively.

The co-reactant is provided in a quantity that is substantially stoichiometric relative to the aryl halide. Quantities of co-reactant from about 0.9 mol to about 2 mols per mol of aryl halide are satisfactory.

The aryl halide is carbonylated by reaction under carbonylation conditions with carbon monoxide in the presence of the co-reactant, a weak base and the catalyst system. The base serves to neutralize the hydrogen halide formed during the carbonylation and bases which are compatible with the reactants and catalyst system are useful in the reaction. Inorganic salts of strong bases and weak acids are useful as bases in the process, e.g., sodium acetate, sodium bicarbonate and potassium borate. Preferred bases, however, are organic tertiary amines of up to 15 carbon atoms such as trimethylamine, triethylamine, diethylbutylamine, dimethylaniline tripropylamine and dimethyloctylamine. Particularly preferred bases are trialkylamines such as trimethylamine, triethylamine, dimethylpentylamine and tripropylamine. Most preferred as the base is triethylamine.

The base is employed in a quantity sufficient to neutralize the hydrogen halide formed by the carbonylation process and any other acidic material formed during the reaction as when the co-reactant is water and the product is a carboxylic acid. Quantities of base from about 0.9 mol to about 2.5 mols per mol of aryl halide are suitable.

The catalyst system of the invention is formed from a source of palladium and a bidentate phosphine ligand of particular structure. The palladium source is suitably a palladium carboxylate and palladium acetate, palladium propionate, palladium butyrate and palladium hexanoate are satisfactory. Palladium acetate is particularly preferred as the source of palladium.

The bidentate phosphine ligand has at least one monovalent phosphorus substituent which is an aromatic substituent containing an electron-withdrawing group substituted on an aromatic ring carbon atom. One class of such bidentate phosphine ligands has up to 40 carbon atoms and is illustrated by the formula

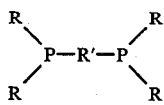  (I)

wherein R independently is aromatic of up to 15 carbon atoms inclusive substituted on at least one aromatic ring carbon atom by an electron-withdrawing group such as alkoxy or dialkylamino, and R' is a hydrocarbyl linking group of up to 10 carbon atoms inclusive with from 2 to 4 carbon atoms inclusive in the bridge. Within each R group, the electron-withdrawing substituent is located on a ring carbon atom ortho or para to the carbon atom through which the R group is bound to the phosphorus. Preferred R groups have at least one electron-withdrawing group in the ortho position relative to the R/phosphorus bond and are illustrated by 2-methoxyphenyl, 2-propoxyphenyl, 2,4-diethoxyphenyl, 2-dimethylaminophenyl, 2-ethylmethylaminophenyl and 2,4,6-trimethoxyphenyl. Best results are obtained if each R is 2-alkoxyphenyl, particularly 2-methoxyphenyl. Suitable R' groups are illustrated by 1,2-ethylene, 1,3-propylene, 1,4-butylene, 2,2-dimethyl-1,3-propylene and 2,3-dimethyl-1,4-butylene. The preferred R' group is 1,3-propylene and the preferred phosphine ligand is 1,3-[di(2-methoxyphenyl)phosphino]propane.

The bidentate phosphorus ligand is employed in a quantity of from about 0.1 mol to about 10 mols of ligand per mol of palladium. Preferred quantities of phosphine ligand are from about 0.5 mol to about 5 mols of ligand per mol of palladium. The catalyst system is employed in a catalytic quantity relative to the aryl halide reactant. Quantities of catalyst system sufficient to provide from about $1\times10^{-7}$ mol of palladium per mol of aryl halide are satisfactory. Preferred quantities of catalyst system are sufficient to provide from about $1\times10^{-6}$ mol to about $1\times10^{-2}$ mol of palladium per mol of aryl halide.

The carbonylation is a homogeneous reaction or a heterogeneous reaction but preferably is conducted as a homogeneous process in an aprotic solvent. Suitable aprotic solvents include ketones such as acetone and methyl ethyl ketone, ethers such as diethylene glycol dimethyl ether, tetrahydrofuran anisole and diphenyl ether, aromatic hydrocarbons such as toluene and xylene, nitriles such as acetonitrile and benzonitrile, and esters such as ethyl butyrate and methyl benzoate. Acyclic ethers are the preferred solvents and particularly preferred is diethylene glycol dimethyl ether (diglyme).

The carbonylation conditions include an elevated temperature and typically an elevated pressure. Temperatures from about 70° C. to about 200° C. are useful with preferred temperatures being from about 90° C. to about 150° C. Reaction pressures are from about 1 bar to about 100 bar, although pressures from about 10 bar to about 70 bar are more often used.

The process of the invention provides the products normally produced by aryl halide production in the presence of the co-reactant. Aldehydes are produced when the co-reactant is hydrogen, acids are produced in the presence of water as co-reactant, alcohol or phenol co-reactants lead to production of esters and amides are formed when an amine is a co-reactant. However, the process provides good yields of carbonylated product at a relatively high rate of conversion and selectivity, even when the aryl chlorides are used which are known to be unsuitable in similar processes.

The invention is further illustrated by the following Comparative Examples (not of the invention) and the following Illustrative Embodiments which should not be regarded as limitations.

ILLUSTRATIVE EMBODIMENT I

To an autoclave of 250 ml capacity equipped with a mechanical stirrer were charged 0.5 mmol palladium acetate, 1 mmol 1,3-bis[di(2-methoxyphenyl)phosphino]propane, 25 ml ethanol, 15 ml chlorobenzene and 25 ml trimethylamine. The air present in the autoclave was evacuated and carbon monoxide was introduced until a pressure of 50 bar was reached. The autoclave was then sealed and heated to 155° C. After a reaction time of 5 hours, a sample of the product mixture was removed and analyzed by gas-liquid chromatography (glc). It was found that the conversion of chlorobenzene was 10.5% with a selectivity to ethyl benzoate that was essentially quantitative.

COMPARATIVE EXAMPLE I

The procedure of Illustrative Embodiment I was substantially repeated except that the 1,3-bis[di(2-methoxyphenyl)phosphino]propane was replaced by 1,3-bis(diisopropylphenylphosphino)propane. The conversion of chlorobenzene was 15%.

ILLUSTRATIVE EMBODIMENT II

The procedure of Illustrative Embodiment I was substantially repeated except that the chlorobenzene was replaced by 4-methoxychlorobenzene. The conversion to ethyl anisate was 5%.

ILLUSTRATIVE EMBODIMENT III

The procedure of Illustrative Embodiment I was substantially repeated except that the chlorobenzene was replaced by bromobenzene and the reaction period was 2 hours at 150° C. Analysis by glc indicated a quantitative conversion to ethyl benzoate.

ILLUSTRATIVE EMBODIMENT IV

To an autoclave of 250 ml capacity equipped with a mechanical stirrer were charged 0.5 mmol palladium acetate, 1 mmol 1,3-bis[di(2-methoxyphenyl)phosphino]propane, 10 ml methanol, 10 ml chlorobenzene, 7.5 g sodium acetate and 50 ml N-methylpyrrolidone. Air was evacuated from the autoclave and carbon monoxide was introduced until a pressure of 50 bar was reached. The autoclave was sealed and then heated to 150° C. After a reaction period of 15 hours, a sample of the product mixture was withdrawn and subjected to glc analysis. The conversion of chlorobenzene was 10.3% with a 100% selectivity to methyl benzoate.

ILLUSTRATIVE EMBODMENT V

The procedure of Illustrative Embodiment III was substantially repeated using a catalyst system formed from 0.5mmol palladium acetate, 2 mmol 1,3-bis[di(2- methoxyphenyl)phosphino]propane and 1 mmol trifluoromethanesulfonic acid.

COMPARATIVE EXAMPLE II

The procedure of Illustrative Embodiment III was substantially repeated except that the 1,3-bis[di(2-methoxyphenyl)phosphino]propane was replaced by 1,3-bis(diphenylphosphino)propane. After the 15-hour reaction period, only traces of methyl benzoate could be found by glc analysis of the product mixture.

What is claimed is:

1. In the process of carbonylating an aryl halide by contacting the aryl halide under carbonylation conditions with carbon monoxide and a hydrogen-containing co-reactant in the presence of a base and a catalyst system formed from a source of palladium and a phosphine ligand, the improvement of using as the phosphine ligand a bidentate phosphine ligand wherein at least one monovalent phosphorus substituent is aromatic substituted on a ring carbon atom by an electron-withdrawing group.

2. The process of claim 1 wherein the bidentate ligand is of the formula

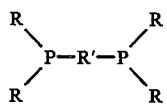

wherein R independently is aromatic of up to 15 carbon atoms inclusive substituted on at least one carbon atom ortho or para to the ring carbon atom through which the R is bonded to the phosphorus with an electron-withdrawing group, and R' is hydrocarbyl linking group of up to 10 carbon atoms inclusive with from 2 to 4 carbon atoms inclusive in the bridge.

3. The process of claim 2 wherein the electron-withdrawing group is alkoxy or dialkylamino.

4. The process of claim 3 wherein R' is 1,3-propylene.

5. The process of claim 4 wherein the electron-withdrawing group is alkoxy.

6. The process of claim 5 wherein R is 2-alkoxyphenyl.

7. The process of claim 5 wherein R is 2-methoxyphenyl.

8. In the process of carbonylating an aryl chloride by contacting the aryl chloride under carbonylating conditions with carbon monoxide and hydrogen or alkanol in the presence of a base and a catalyst system formed from a source of palladium and a phosphine ligand, the improvement of using as the ligand a bidentate phosphine ligand of the formula

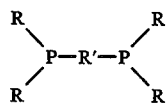

wherein R independently is aromatic substituted on at least one ring carbon atom ortho or para to the ring carbon atom through which the R is bonded to the phosphorus with alkoxy or dialkylamino, and R' is a divalent hydrocarbyl linking group of up to 10 carbon atoms inclusive with from 2 to 4 carbon atoms inclusive in the bridge.

9. The process of claim 8 wherein R' is 1,3-propylene.

10. The process of claim 9 wherein R is 2-alkoxyphenyl.

11. The process of claim 10 wherein R is 2-methoxyphenyl.

* * * * *
* * * * *